United States Patent
Mackenzi et al.

(10) Patent No.: US 8,282,652 B2
(45) Date of Patent: Oct. 9, 2012

(54) FORCE-CONTROLLED AUTODISTRACTION

(75) Inventors: William Mackenzi, Montchanin, DE (US); Tariq Rahman, Moylan, PA (US); Robert Akins, Newark, DE (US); Alastair Younger, Vancouver (CA)

(73) Assignee: The Nemours Foundation, Jacksonville, FL (US)

( * ) Notice: Subject to any disclaimer, the term of this patent is extended or adjusted under 35 U.S.C. 154(b) by 699 days.

(21) Appl. No.: 11/498,284

(22) Filed: Aug. 2, 2006

(65) Prior Publication Data
US 2008/0051779 A1 Feb. 28, 2008

(51) Int. Cl.
A61B 17/00 (2006.01)

(52) U.S. Cl. ...................................... 606/105

(58) Field of Classification Search ............. 606/105, 606/56–59, 90, 102
See application file for complete search history.

(56) References Cited

U.S. PATENT DOCUMENTS

| | | | |
|---|---|---|---|
| 4,501,266 A | 2/1985 | McDaniel | 128/69 |
| 4,615,338 A | 10/1986 | Ilizarov et al. | 128/92 |
| 4,973,331 A | 11/1990 | Pursley et al. | 606/54 |
| 5,156,605 A | 10/1992 | Pursley et al. | 606/54 |
| 5,180,380 A * | 1/1993 | Pursley et al. | 606/54 |
| 5,207,676 A * | 5/1993 | Canadell et al. | 606/54 |
| 5,314,426 A * | 5/1994 | Pohl et al. | 606/58 |
| 5,334,202 A * | 8/1994 | Carter | 606/58 |
| 5,350,379 A | 9/1994 | Spievack | 606/63 |
| 5,415,660 A * | 5/1995 | Campbell et al. | 606/62 |
| 5,429,638 A | 7/1995 | Muschler et al. | 606/60 |
| 5,437,668 A * | 8/1995 | Aronson et al. | 606/57 |
| 5,454,810 A * | 10/1995 | Pohl et al. | 606/59 |
| 5,536,269 A | 7/1996 | Spievack | 606/63 |
| 5,601,551 A * | 2/1997 | Taylor et al. | 606/54 |
| 5,626,579 A * | 5/1997 | Muschler et al. | 606/60 |
| 5,626,581 A | 5/1997 | Staehlin et al. | 606/63 |
| 5,697,165 A * | 12/1997 | Richardson | 33/512 |
| 5,704,938 A | 1/1998 | Staehlin et al. | 606/62 |
| 5,961,553 A * | 10/1999 | Coty et al. | 606/62 |
| 5,976,125 A * | 11/1999 | Graham | 606/32 |
| 6,017,341 A * | 1/2000 | Windhagen et al. | 606/56 |
| 6,022,349 A * | 2/2000 | McLeod et al. | 606/58 |
| 6,033,412 A * | 3/2000 | Losken et al. | 606/105 |
| 6,336,929 B1 | 1/2002 | Justin | 606/63 |
| 6,673,079 B1 | 1/2004 | Kane | 606/105 |
| 6,706,042 B2 * | 3/2004 | Taylor | 606/57 |
| 6,761,723 B2 | 7/2004 | Buttermann et al. | 606/79 |
| 6,827,721 B2 * | 12/2004 | Perren et al. | 606/102 |
| 6,849,076 B2 * | 2/2005 | Blunn et al. | 606/105 |
| 2003/0004518 A1 * | 1/2003 | Perren et al. | 606/102 |
| 2003/0144669 A1 * | 7/2003 | Robinson | 606/90 |
| 2004/0030395 A1 * | 2/2004 | Blunn et al. | 623/18.12 |

* cited by examiner

Primary Examiner — Kevin T Truong
Assistant Examiner — Christopher Beccia
(74) Attorney, Agent, or Firm — Drinker Biddle & Reath LLP

(57) ABSTRACT

Force-controlled autodistraction for lengthening a bone is disclosed. A distractor is coupled to first and second fixators that are coupled to first and second portions of the bone, respectively, on opposite sides of an osteotomy of the bone. A motor produces a motion of the first fixator relative to the second fixator such that the first portion of the bone is distracted from the second portion of the bone. A force sensor measures a resistant force to the motion, and a distractor displacement sensor measures a distractor displacement. A controller is operably coupled to the force sensor, the distractor displacement sensor, and the motor. The controller is configured to determine a variable limb stiffness using the resistant force, the distractor displacement, and a known distractor stiffness of the distractor, and to adjust a gain of the motor such that the variable limb stiffness matches a desired limb stiffness.

21 Claims, 3 Drawing Sheets

FORCE-CONTROLLED AUTODISTRACTION

FIELD OF THE INVENTION

The present invention is directed to medical equipment and methods used for the treatment of bone defects and injuries, and, more particularly, the invention is directed to autodistraction systems and methods for lengthening a bone.

BACKGROUND OF THE INVENTION

Limb lengthening devices known as distractors are used in the treatment of bone defects and injuries, and for lengthening bone in connection with osteotomy (for example, complete osteotomy or corticotomy).

A distractor has a length that is adjustable (e.g., expandable or telescoping). The distractor generally includes, proximate to each end of the length, one or more fixators for attaching the distractor to a bone in a limb of a subject (e.g., a patient). The distractor is typically applied by affixing each fixator to the bone (such as by using pins, screws, Kirschner wires, and the like), such that each end of the distractor is attached to the bone at an opposite side of a distraction gap created by the osteotomy. The distractor is able to elongate the distance between the fixators at each end of the distractor, thereby applying force or tension to the bone over a period of time, to gradually lengthen the bone in small increments. The bone is lengthened by osteogenesis (i.e., the formation of new bone), bridging the distraction gap. In a typical example, a treatment regime may call for a predetermined distraction rate of one millimeter per day (mm/day) during a treatment period.

The rhythm of distraction, i.e., the frequency of lengthening the distractor, is directly related to the speed of osteogenesis. Some distractors are configured to be lengthened periodically, e.g., by manually adjusting the length of the distractor a number of times each day during the treatment period, so as to increase the distraction by a given amount with each adjustment. Other distractors, generally known as automatic distractors or autodistractors, are configured with a motor that is able to continuously increase the length of the distractor at a predetermined distraction rate during the treatment period. Autodistractors that produce a continuous and gradual distraction (e.g., elongating the distractor at a predetermined distraction rate of about 1.0 mm/day) have been found to produce more rapid osteogenesis than distractors that are periodically lengthened (e.g., several times a day).

Distractors may be instrumented with a displacement sensor for determining actual distractor displacement; that is, the displacement sensor allows a practitioner (e.g., a physician, surgeon, clinician, or researcher) to monitor changes in the length of the distractor or the distance between the fixators. An autodistractor may also be instrumented with a force sensor (e.g., a strain gauge, or a load cell) for sensing the force applied by the distractor to the bone, and with a controller able to disable the motor if a predetermined threshold of force has been exceeded.

To achieve a desired elongation rate, autodistractors have applied a constant gain (i.e., constant voltage) to the motor, producing a constant force to elongate the bone. The desired rate of distraction is set by a practitioner, and this is used to determine the constant voltage applied to the motor. The actual rate of bone distraction may or may not mimic the desired rate of distraction, depending upon factors including resistant force encountered in the limb. The motor drives at its specified rate regardless of the resistant force it encounters. As a result, inappropriate forces may develop in the distraction zone. These forces could either be too high or too low. If high forces are allowed to build up, this could indicate that there is premature consolidation, or conversely, that there is too much separation resulting in high stresses on the surrounding soft tissue. In the case of low forces, this might indicate that there is insufficient bone formation in the distraction gap.

SUMMARY OF THE INVENTION

Force-controlled autodistraction systems and methods are provided. In an illustrative implementation, a distractor is coupled to a first fixator and to a second fixator distal to the first fixator. The distractor has a known distractor stiffness. The first fixator is configured to be coupled to a first portion of the bone, and the second fixator is configured to be coupled to a second portion of the bone. The first and second portions are on opposite sides of an osteotomy of the bone. A motor is controllable to produce a motion of the first fixator relative to the second fixator, such that the first portion of the bone is distracted from the second portion of the bone. A force sensor is configured to measure a resistant force to the motion, and a distractor displacement sensor is configured to measure a distractor displacement. A controller is operably coupled to the force sensor, the distractor displacement sensor, and the motor. The controller is configured to determine a variable limb stiffness using the resistant force, the distractor displacement, and the known distractor stiffness. The controller is further configured to adjust a gain of the motor such that the variable limb stiffness will match a desired limb stiffness.

It is to be understood that both the foregoing general description and the following detailed description are exemplary and explanatory and are intended to provide further explanation of the invention as claimed.

BRIEF DESCRIPTION OF THE DRAWINGS

For the purpose of illustrating the invention, there is shown in the drawings a form that is presently preferred; it being understood, however, that this invention is not limited to the precise arrangements and instrumentalities shown.

DETAILED DESCRIPTION OF THE INVENTION

Overview

Aspects of the present invention provide an autodistractor able to dynamically vary a distraction rate of a bone in a limb of a subject, e.g., in response to resistance encountered in the limb during distraction, to achieve a desired limb stiffness. By measuring the stiffness of the limb, and using the measurement to control the gain in the motor, a more successful distraction may be provided. A practitioner also can obtain additional feedback on the state of the lengthening, which may be useful for determining whether there is too much force or too little force, or whether the bone has appropriately healed.

In further aspects of the invention, an autodistractor is provided with a sensor and a controller able to vary a distraction rate, based on a force developed during distraction. In contrast to fixed displacement-driven distraction, it is believed that embodiments of variable distraction limb lengthening can offer a subject greater convenience and less pain during distraction. Aspects of variable distraction limb lengthening can provide a more optimal lengthening than fixed-displacement modalities.

Embodiments of the invention include a closed-loop feedback system in the autodistractor for determining a variable limb stiffness ($K_{leg}$) from the use of a resistant force measurement (F), a known distractor displacement (x), and a known distractor stiffness ($K_d$), and for adjusting a gain of the motor in the autodistractor, so that the variable limb stiffness ($K_{leg}$) will match a desired limb stiffness. The distraction rate, i.e., the rate at which the rotation of the motor causes the distractor to lengthen, can be adjusted by varying the gain. The distraction rate can be adjusted based on the difference between the variable limb stiffness and the desired limb stiffness.

In some embodiments, aspects of the invention are able to use measured force information to ensure that a predetermined value of the resistant force measurement is not exceeded, which can be useful both as a safety mechanism and for implementing a control algorithm using calculated stiffness to dictate an optimal lengthening regime.

Illustrative Autodistraction Environment

Figure 1A:
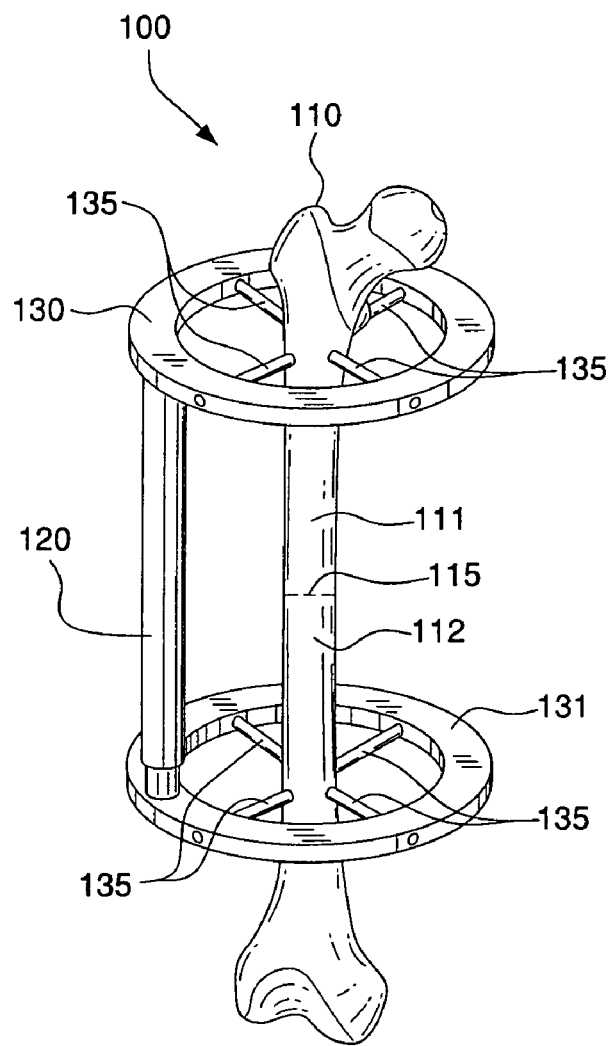
FIG. 1A is a depiction of an exemplary autodistractor coupled to a bone, in accordance with an embodiment of the invention.
Figure 1B:
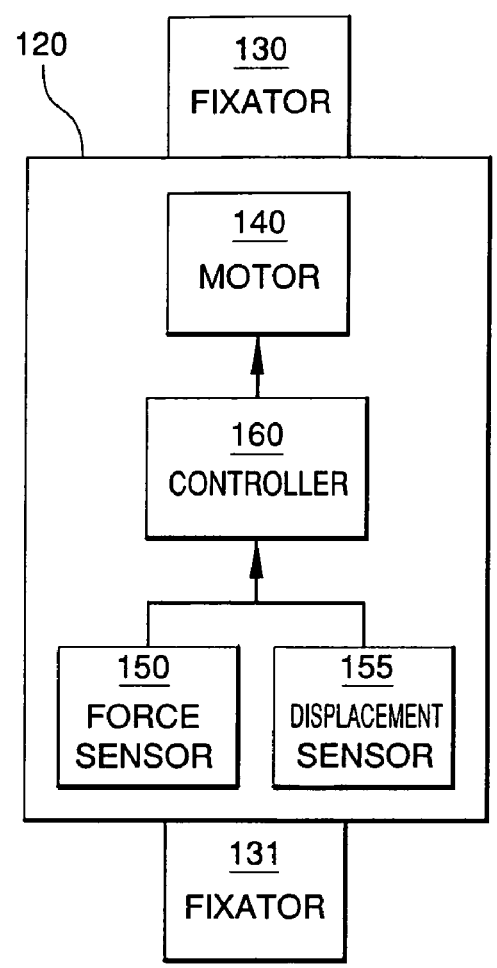
FIG. 1B is a block diagram showing the cooperation of exemplary components of an exemplary autodistractor, in accordance with an embodiment of the invention.

Referring to the drawings, in which like reference numerals indicate like elements, FIG. 1A depicts an exemplary force-controlled autodistractor 100 for lengthening a bone 110 in accordance with herein-described systems and methods. FIG. 1B is a block diagram showing the cooperation of exemplary components of an exemplary force-controlled autodistractor 100.

The bone 110 is in a limb (not shown) of a subject (not shown). The subject (e.g., a patient) may be a human or animal. While the illustrative bone 110 shown in FIG. 1A represents a human tibia, the bone 110 may be a tibia, fibula, femur, radius, ulna, humerus, or any other bone (e.g., of a limb or digit) deemed by a practitioner to be suitable for lengthening by distraction.

The autodistractor 100 comprises at least one distractor, such as distraction mechanism 120. Distraction mechanism 120 is coupled to a first fixator 130. Distraction mechanism 120 is also coupled to a second fixator 131 distal to the first fixator 130. Distraction mechanism 120 is configured to permit linear motion of the first fixator 130 relative to the second fixator 131, e.g., substantially parallel to an axis of the distraction mechanism 120. In some embodiments, the linear motion may be, during use, substantially parallel to the length of the bone 110.

The first fixator 130 is configured to be coupled to a first portion 111 of the bone 110, and the second fixator is configured to be coupled to a second portion 112 of the bone 110.

The first portion 111 and second portion 112 of the bone 110 are on opposite sides of an osteotomy 115 of the bone 110. The osteotomy 115 may be, for example, a complete osteotomy or a corticotomy. The osteotomy 115 may be performed at any medically desirable position and angle on the bone 110, and may be performed on the bone 110 at any medically desirable time prior to commencing distraction of the bone 110; i.e., before, during, or after coupling the fixators 130, 131 to the bone 110.

In an exemplary embodiment, the fixators 130, 131 are coupled to the bone 110 by a plurality of fasteners 135. For example, fasteners 135 may be pins, or other means for coupling the fixators 130, 131 to the bone 110 may be used; for example, a plurality of screws, wires (e.g., Kirschner wires), or any other suitable devices may be used for coupling the fixators 130, 131 to the bone 110. Any number of fasteners 135 or other suitable coupling devices may be used in autodistractor 100 for practicing the invention, as may be medically appropriate for distracting the bone 110.

A motor 140 is controllable to produce a motion of the first fixator 130 relative to the second fixator 131 such that the first portion 111 of the bone 110 is distracted from the second portion 112 of the bone 110. Depending on the configuration of the distraction mechanism 120, the relative motion may be produced by applying force to either of the first fixator 130 or the second fixator 131, or to both fixators 130, 131, so as to increase the distance between the fixators 130, 131.

A force sensor 150 is configured to measure a resistant force to the motion. The force sensor 150 is able to directly measure the resistant force against the motion. In a further embodiment, an exemplary force sensor 150 comprises a load cell or strain gauge. Another embodiment includes a force sensor 150 having an appropriate size and dynamic range, placed into a housing of the autodistractor 100.

A distractor displacement sensor 155 is configured to measure a distractor displacement of the distraction mechanism 120, e.g., a length (or change in length) of distraction mechanism 120, or a distance (or change in distance) between the fixators 130, 131. In one embodiment, an exemplary distractor displacement sensor 155 comprises a linear variable displacement transducer (LVDT).

A controller 160 is operably coupled (for example, electrically coupled, mechanically coupled, or wirelessly coupled) to the force sensor 150, the distractor displacement sensor 155, and the motor 140. The controller 160 is configured to adjust a gain of the motor 140, e.g., by adjusting voltage of an electrical input to the motor 140.

Controller 160 may, for example, comprise one or more microprocessors. In some embodiments, an exemplary controller 160 may comprise a preliminary breadboard circuit; once the preliminary breadboard circuit has been tested with the force sensor 150, a suitable integrated circuit for use in controller 160 can readily be designed and manufactured. Operation of an exemplary controller 160 can be controllable using an computer system (not shown), e.g., a personal computer using virtual instrument software such as Labview.

In some embodiments, the controller 160 may be configured to provide telemetry, which can be transmitted to the practitioner (e.g., via wired or wireless communication, or via a communication network such as the Internet). The use of telemetry may facilitate assessment of a subject's progress, and may reduce the need for a visit by the subject to a medical or laboratory facility.

Numerous possible configurations of the distraction mechanism 120 and the autodistractor 100 are suitable for practicing aspects of the present invention. Commercially available motorized distractors may be adapted to practice aspects of the invention. In some embodiments, the autodistractor 100 may comprise a commercially available autodistractor (for example, an automated distractor device available from Autogenesis, Inc.) reconfigured to practice aspects of the present invention, e.g., by instrumenting the commercially available autodistractor with a force sensor 150, and by adding or reconfiguring a controller 160. An exemplary position of the force sensor 150 can be inside a housing for the distraction mechanism 120; in an illustrative example, an automated distractor device available from Autogenesis, Inc. may in some embodiments be instrumented with force sensor 150 positioned next to a main gear of the device.

Examples of suitable autodistractors for use in embodiments of the present invention include those disclosed by Pursley, et al., in U.S. Pat. Nos. 4,973,331 and 5,180,380, which are herein incorporated by reference in their entirety. However, aspects of the invention may readily be used in connection with autodistractors of numerous other types. Further examples of autodistractors that may be suitably adapted for use with aspects of the invention include internal autodistractors that are configured to be placed wholly or partially within the bone 110, and external autodistractors having external fixators 130, 131 (e.g., Ilizarov circular fixators or uniplanar fixators) for attaching the autodistractor 100 to the bone 110. In adapting a commercially available autodistractor, the controller 160 may have to be redesigned, e.g., by configuring a circuit board to accept input from the force sensor 150.

A further exemplary distraction mechanism 120 may comprise guide rods (not shown) for guiding the motion of the first fixator 130 relative to the second fixator 131. A still further exemplary distraction mechanism 120 may comprise one or more rods (not shown), such as a telescoping, extensible, or slidable rod, for elongating the distraction mechanism 120 so that separation between the first and second fixators 120, 121 is increased. The exemplary distraction mechanism 120 generally includes means for translating a rotary motion of a motor 140 into the linear motion of the first fixator 130 relative to the second fixator 131; for example, one or more gears, screws, cables, or the like (not shown) may be used to couple the motor 140 to the first fixator 130.

It is appreciated that the exemplary distraction mechanism 120 and fixators 130, 131 discussed herein are merely illustrative of an autodistractor 100 in which the herein described systems and methods may operate and does not limit the implementation of the herein described systems and methods in an autodistractor 100 having differing components and configurations, as the inventive concepts described herein may be implemented using various distraction mechanisms 120 and fixators 130, 131 having various components and configurations.

Determination of Variable Limb Stiffness

Figure 2:
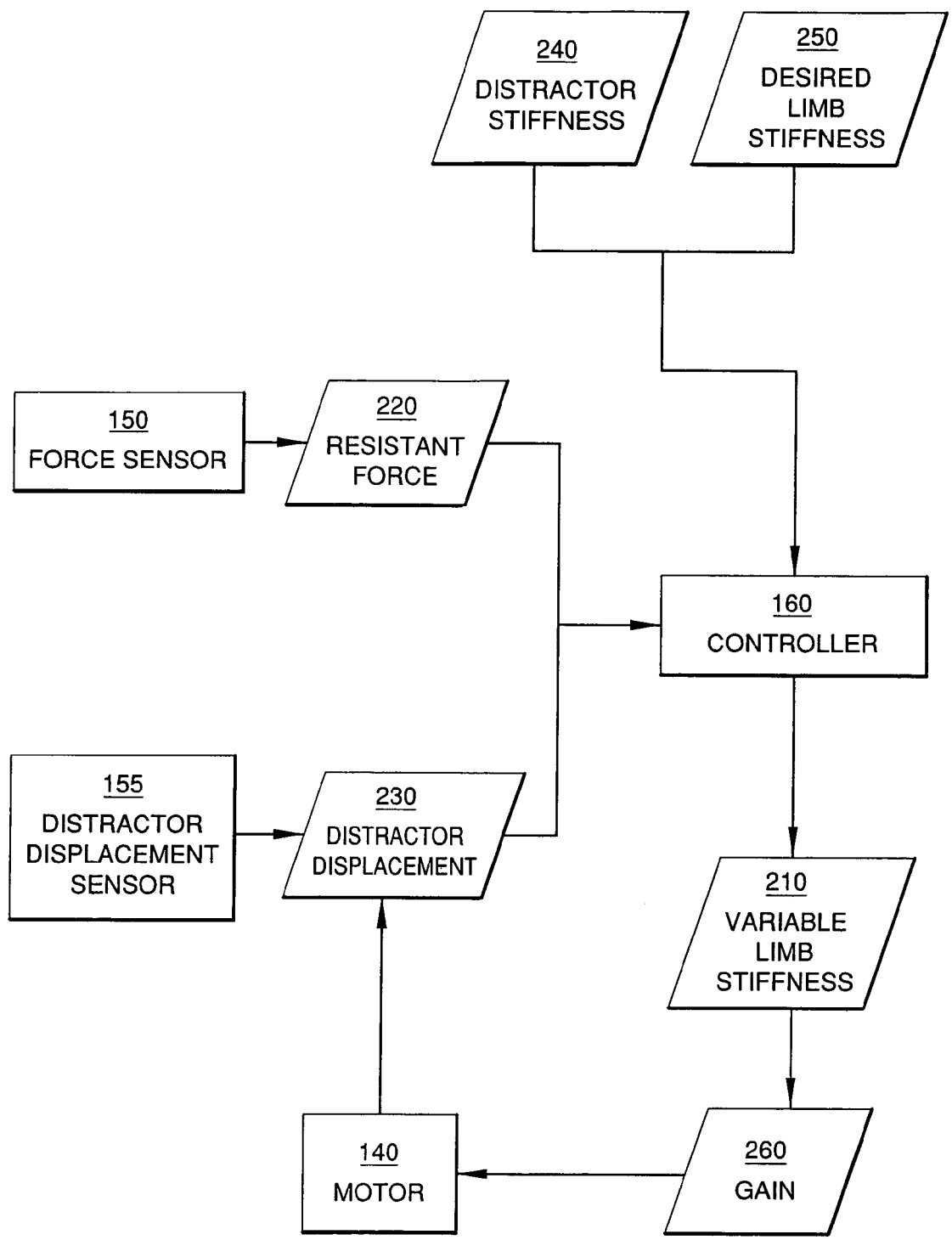
FIG. 2 is a diagram illustrating data flow for an exemplary controller for practicing an embodiment of the invention.

FIG. 2 is a diagram illustrating data flow for an exemplary controller 160 for practicing an embodiment of the invention. The controller 160 is configured to determine a variable limb stiffness 210 using the resistant force 220, the distractor displacement 230, and the distractor stiffness 240. The controller 160 is configured to adjust a gain 260 of the motor 140 such that the variable limb stiffness 210 will match a desired limb stiffness 250. A closed-loop feedback system is thereby provided in the autodistractor 100.

In some embodiments, the controller 160 may be also configured to provide telemetry to a practitioner. Such telemetry may, for example, include one or more values selected from a group consisting of the variable limb stiffness 210, the resistant force 220, the distractor displacement 230, the distractor stiffness 240, the desired limb stiffness 250, and the gain 260.

The resistant force 220 is force encountered in the limb that resists (e.g., pushes back against) the distraction of the bone 110 by the autodistractor 100. There is some controversy as to whether resistant force 220 is transmitted primarily through regenerate bone tissue or surrounding soft tissue. In addition to clinical use, the autodistraction system of the invention may be used to measure the variable limb stiffness 210 in vivo, thereby facilitating studies of the origin of the resistant force 220. Such measurements may assist in determining the relative contribution of the two tissues. Further aspects of the invention can offer the potential to perform measurements of resistant force 220 during minute oscillatory movements that will allow non-radiographic assessments of bony and soft tissue.

The variable limb stiffness 210 can be determined using the following equation:

$$K_{leg} = (F/x) - K_d$$

The same equation may also be expressed as:

$$F = (K_{leg} + K_d)x$$

In the foregoing equations, $K_{leg}$ represents the variable limb stiffness 210, i.e., stiffness of the limb. F represents the resistant force 220, which can be directly measured by the force sensor 150. x represents the distractor displacement 230, which may be measured by distractor displacement sensor 155. $K_d$ represents the distractor stiffness 240, which will be known prior to actual use of the autodistractor 100 on a bone 110, as further discussed below. Stiffness (such as variable limb stiffness 210, distractor stiffness 240, and desired limb stiffness 250) can be expressed in newtons per millimeter (N/mm). Resistant force 220 can be expressed in newtons, and distractor displacement 230 can be expressed in millimeters.

Using either of the foregoing equations, the variable limb stiffness 210 of the leg may be determined, so that it can be compared against the desired limb stiffness 250. The difference, if any, between the variable limb stiffness 210 and desired limb stiffness 250 determines changes that the controller 160 can apply to the motor 140. Accordingly, if the variable limb stiffness 210 is too high, the distraction rate may be decreased, and if the variable limb stiffness 210 is too low, the distraction rate may be increased.

An exemplary controller 160 is able to convert the difference between variable limb stiffness 210 and desired limb stiffness 250 to a gain 260. An exemplary gain 260 is a voltage signal to the motor 140, which may be increased or decreased by the controller 160, thereby increasing or decreasing the distraction rate, i.e., the rate of change in the distractor displacement 230.

In some embodiments, an initial gain 260 can be applied to the motor 140 to produce an initial distraction rate, such as a distraction rate of one millimeter per day, which is typically used in a clinical environment. The gain 260 can then be adjusted by the controller 160. For example, in further embodiments, the resistant force 220 encountered can be limited to a band. In such embodiments, if the resistant force 220 measured in the autodistractor 100 were to vary outside an upper or lower limit of the band, the gain 260 can be altered appropriately. During use of an exemplary autodistractor 100, if the resistant force 220 becomes too high, then the distraction rate will be slowed down (e.g., by reducing the gain 260), and if the resistant force 220 becomes too low, the distraction rate will be increased (e.g., by increasing the gain 260). In still further embodiments, an audible signal can be sounded if the resistant force 220 varies outside an upper or lower limit of the band. An illustrative estimate of the band can be based on resistant forces 220 measured by previous ovine experiments, in which the peak resistant force 220 reported is 200-300N in sheep tibia during lengthening.

During use of the autodistractor 100 in the subject, the force sensor 220 may sense a value of resistant force 220 that a skilled practitioner is able to determine to be high. A high value of resistant force 220 could indicate that there is premature consolidation, or conversely that there is too much separation resulting in high stresses on the surrounding soft tissue. In each case, as may be determined by the practitioner, a programmed response of the controller 160 may in some embodiments be different; i.e., in the first case, the rate of distraction may be increased to avoid impending consolidation, and in the second, the rate of distraction may be decreased to avoid damage to the soft tissue. In these and other situations, the practitioner can gauge the forces in the distraction environment, e.g., to head off potential problems, and to guide the distraction based on optimal stiffness profiles for determining desired limb stiffness 250, such as may be determined by the practitioner.

Distractor Stiffness

The autodistractor 100 will have a known distractor stiffness 240; for example, stiffness that is attributable to bending of the distraction mechanism 120 and the fasteners 135 as a unit. The distractor stiffness 240 will be measured without attaching the fixators 130, 131 to the bone 110; for example, a manufacturer of the autodistractor 100 may measure or calculate the value of the distractor stiffness 240. The distractor stiffness 240 may be a fixed characteristic of a particular model or design of an embodiment of the autodistractor 100, or the distractor stiffness 240 may be individually measured or tested for each unit of the autodistractor 100 prior to use of the autodistractor 100 on a subject.

In an exemplary embodiment suitable for determining the distractor stiffness 240 of the autodistractor 100, the distraction mechanism 120 of the autodistractor 100 may be mounted on a test-bed (not shown) and prepared for elongation. Mounting may be performed by coupling the fixators 130, 131 to the test-bed using fasteners 135 that are identical to the fasteners 135 used for coupling the fixators 130, 131 to bone 100 in surgery, thus allowing a stiffness measurement for the combination of the distractor mechanism 120 and fasteners 135. The test-bed can comprise a first and second artificial bone segment (not shown) for modeling the first portion 111 and second portion 112 of a bone 110. The artificial bone segments can be, for example, aluminum rods. The second artificial bone segment may be clamped in place and the first artificial bone segment may be allowed to move in response to the elongation. A tension spring (not shown) may connect the artificial bone segments to mimic the resistant force 220 in the limb, and a linear variable displacement transducer (LVDT) (not shown) may be fitted between the artificial bone segments. The LVDT may be used to measure the distractor displacement 230 between the artificial bone segments, which may then be used to verify the stiffness of the autodistractor 100. The distractor stiffness 240 may be measured a priori by suspending known weights from fasteners 135 (e.g., at the end of the fasteners 135) that are coupled to one or more of the artificial bone segments, and measuring the distractor displacement 230 with the LVDT.

Desired Limb Stiffness

The desired limb stiffness 250 is predetermined, e.g., by a skilled practitioner, prior to the use of the autodistractor 100. In some embodiments, the desired limb stiffness 250 is individually predetermined for a particular subject (not shown) prior to the use of the autodistractor 100 with the subject, e.g., based upon matching a clinical profile of the subject with one or more clinical profiles of prior subjects (e.g., test subjects).

Empirical determination of a desired limb stiffness 250 can be based upon research and statistical techniques generally known to those skilled in the art. The desired limb stiffness 250 may be determined based on many factors that can be determined empirically, including the quality of the regenerate bone, speed of procedure, pain to the subject, state of the growth plate, and stretch of muscles.

An empirical determination of optimal values of desired limb stiffness 250 may, for example, be performed using the autodistractor 100 in a number of test subjects (e.g., a large number of animals used for testing the autodistractor 100). Such test subjects may be divided into groups for undergoing distraction of various rates and rhythms using the autodistractor 100. Clinical outcomes in terms of growth plate damage, callous formation, and soft tissue effects can be measured and the optimal desired limb stiffness 250 determined by the skilled practitioner. In some embodiments, the practitioner may determine optimal values of the desired limb stiffness 250 that vary according to clinical profiles of the test subjects. Such values of desired limb stiffness 250 may be used to guide lengthening in later use of the autodistractor 110 in a later subject.

Exemplary Method

Figure 3:
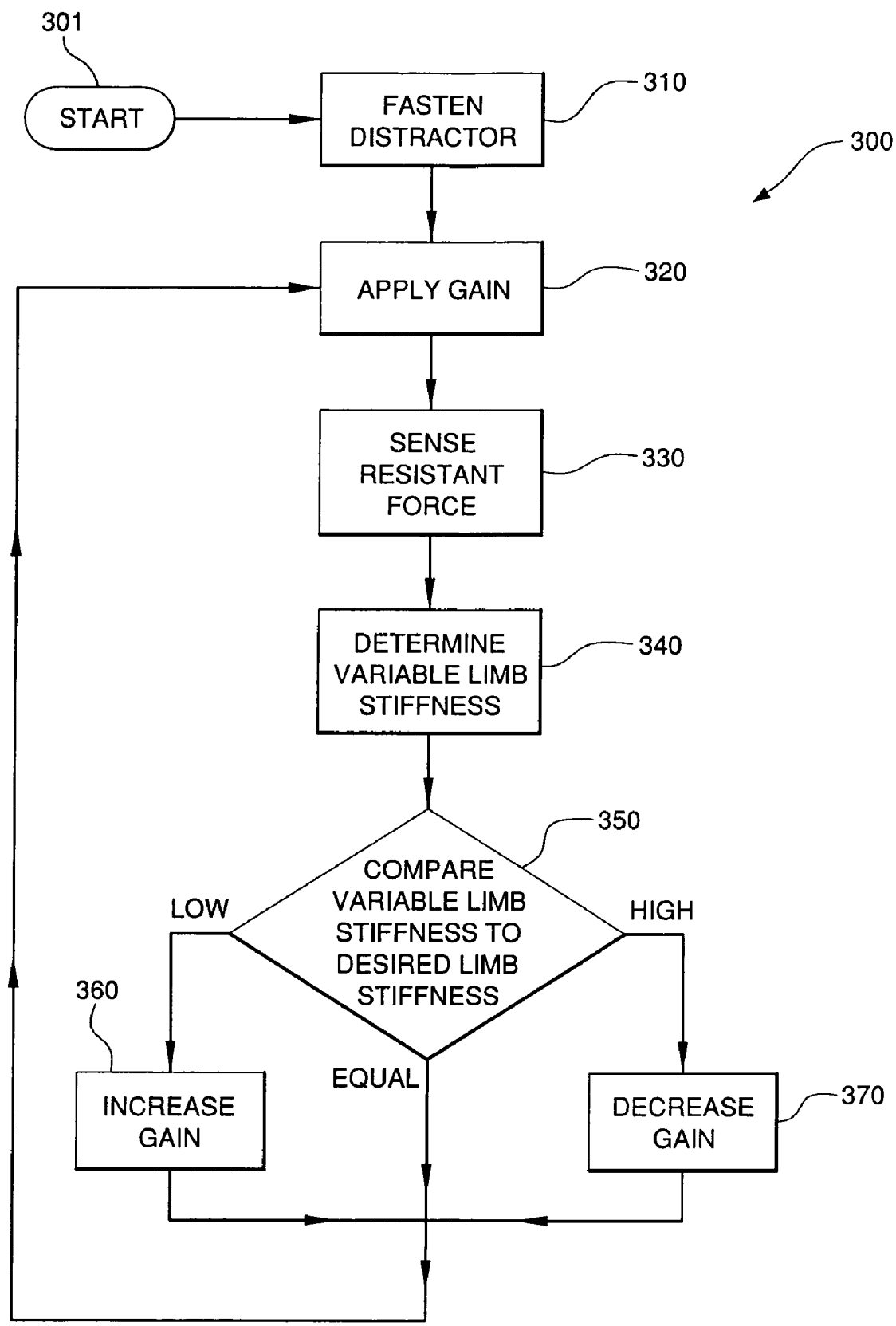
FIG. 3 is a flow chart of a method for force-controlled autodistraction according to an embodiment of the present invention.

FIG. 3 shows the steps of a method 300 for force-controlled autodistraction according to an embodiment of the present invention. The method 300 begins at start block 301, and proceeds to block 310. At block 310, distractor 120 is fastened to bone 110 in a limb of the subject.

At block 320, a gain 260 is applied to motor 140. In some embodiments, the initial value of the gain 260 may be the gain 260 needed to produce a desired distractor displacement rate (e.g., a change in distractor displacement 230 of about one mm/day). The value of the gain 260 can be adjusted during use of the method 300, as discussed below. The method proceeds to block 330.

At block 330, the resistant force 220 in the limb is sensed, using the force sensor 150. At block 340, the variable limb stiffness 210 is determined. As discussed above, controller 160 can be configured to determine variable limb stiffness 210 using the resistant force 220, the distractor displacement 230, and the distractor stiffness 240.

At block 350, a check is performed by the controller 160, to compare the variable limb stiffness 210 to the desired limb stiffness 250. If the variable limb stiffness 210 is lower than the desired limb stiffness 250, the method 300 proceeds to block 360, where the gain 260 is increased by the controller 160, and the method then returns to block 310. If the variable limb stiffness 210 is higher than the desired limb stiffness 250, the method 300 proceeds to block 370, where the gain 260 is decreased by the controller 160, and the method then returns to block 310. If the variable limb stiffness 210 is equal to the desired limb stiffness 250, the method 300 proceeds to block 310.

Although exemplary implementations of the invention have been described in detail above, those skilled in the art will readily appreciate that many additional modifications are possible in the exemplary embodiments without materially departing from the novel teachings and advantages of the invention. Accordingly, these and all such modifications are intended to be included within the scope of this invention. The invention may be better defined by the following exemplary claims.

What is claimed is:

1. A force-controlled autodistraction system for lengthening a bone in a limb, comprising:
   a distractor coupled to a first fixator and to a second fixator, the distractor having a distractor stiffness;
   the first fixator configured to be coupled to a first portion of the bone;
   the second fixator configured to be coupled to a second portion of the bone, the first and second portions being on opposite sides of an osteotomy of the bone;
   a motor controllable to produce a continuous distractor displacement of the first fixator away from the second fixator such that the first portion of the bone is distracted in an axial direction of the bone from the second portion of the bone at a distraction rate;

a distractor displacement sensor configured to measure the distractor displacement in the axial direction;

a force sensor configured to measure a resistant force in the limb caused by the distractor displacement; and a controller operably coupled to the force sensor, the distractor displacement sensor, and the motor, the controller being configured to determine a variable axial limb stiffness based on the resistant force, the distractor displacement, and the distractor stiffness, the variable axial limb stiffness being the resistant force divided by the axial distractor displacement, the controller being further configured to use closed-loop feedback to control the motor to adjust the distraction rate such that the variable axial limb stiffness matches a desired axial limb stiffness by increasing the distraction rate if the variable axial limb stiffness is less than the desired axial limb stiffness and by decreasing the distraction rate if the variable axial limb stiffness is greater than the desired axial limb stiffness.

2. The system of claim 1 wherein the distractor is configured to permit linear motion of the first fixator relative to the second fixator.

3. The system of claim 1 wherein the first fixator is movable, relative to the second fixator, substantially parallel to an axis of the distractor.

4. The system of claim 1 wherein the first fixator is movable, relative to the second fixator, substantially parallel to the length of the bone.

5. The system of claim 1 wherein the fixators are coupled to the bone by a plurality of fasteners.

6. The system of claim 5 wherein the fasteners are selected from a group consisting of pins, screws, and wires.

7. The system of claim 1 wherein the force sensor comprises a strain gauge.

8. The system of claim 1 wherein the force sensor comprises a load cell.

9. The system of claim 1 wherein the distractor displacement sensor comprises a linear variable displacement transducer.

10. The system of claim 1 wherein the controller is configured to provide telemetry comprising one or more values selected from a group consisting of the variable axial limb stiffness, the resistant force, the distractor displacement, the distractor stiffness, the desired axial limb stiffness, and the gain.

11. The system of claim 1 wherein the distractor is configured to be placed external to a limb containing the bone.

12. The system Of claim 1 wherein at least one of the fixators is circular.

13. The system of claim 1 wherein the distractor is configured to be placed within the bone.

14. A force-controlled autodistraction method for lengthening a bone in a subject, comprising:

fastening a distractor to the bone in a limb of the subject, causing a motor to produce a distractor displacement in the distractor in an axial direction for continuous distraction of the bone at a distraction rate, sensing a resistant force in the limb resulting, from the distractor displacement, determining a variable axial limb stiffness based on the resistant force the distractor displacement, and a distractor stiffness, the variable axial limb stiffness being the resistant force divided by the axial distractor displacement, comparing the variable axial limb stiffness to a desired axial limb stiffness as part of a closed-loop feedback control, controlling the motor to increase the distraction rate if the variable axial limb stiffness is lower than the desired axial limb stiffness, and controlling the motor to decrease the distraction rate if the variable axial limb stiffness is higher than the desired axial limb stiffness.

15. The method of claim 14 further comprising determining the desired axial limb stiffness using one or more factors selected from a group consisting of quality of the regenerate bone, speed of procedure, pain to the subject, state of the growth plate, and stretch of muscles.

16. The method of claim 15 wherein determining the desired axial limb stiffness for the subject is performed prior to causing the motor to produce a distractor displacement.

17. The method of claim 14 further comprising sensing the distractor displacement.

18. The method of claim 14 further comprising determining the distractor stiffness.

19. The method of claim 14 wherein causing the motor to produce a distractor displacement comprises applying a voltage as an electrical input to the motor.

20. The method of claim 19, wherein controlling the motor to increase the distraction rate comprises increasing the voltage, and controlling the motor to decrease the distraction rate comprises decreasing the voltage.

21. The method of claim 14 further comprising transmitting to a practitioner one or more values selected from a group consisting of the variable axial limb stiffness, the resistant force, the distractor displacement, the distractor stiffness, the desired axial limb stiffness, and the gain.

* * * * *

UNITED STATES PATENT AND TRADEMARK OFFICE
CERTIFICATE OF CORRECTION

| | | |
|---|---|---|
| PATENT NO. | : 8,282,652 B2 | Page 1 of 1 |
| APPLICATION NO. | : 11/498284 | |
| DATED | : October 9, 2012 | |
| INVENTOR(S) | : William Mackenzie et al. | |

It is certified that error appears in the above-identified patent and that said Letters Patent is hereby corrected as shown below:

On the cover page of the patent, item (75), change "Mackenzi" to --Mackenzie--.

Column 9, lines 48-49, change "Of" to --of--.

Column 10, line 9, delete the "," after the word "resulting".

Column 10, line 12, insert a --,-- after the word "force".

Signed and Sealed this
Twenty-seventh Day of November, 2012

David J. Kappos
*Director of the United States Patent and Trademark Office*